United States Patent
Ahmed et al.

(10) Patent No.: US 10,736,843 B1
(45) Date of Patent: Aug. 11, 2020

(54) IN SITU GELLING COMPOSITION CONTAINING TOCOPHEROL-LOADED MICELLES AS AN INTRANASAL DRUG DELIVERY SYSTEM

(71) Applicant: King Abdulaziz University, Jeddah (SA)

(72) Inventors: Tarek A. Ahmed, Jeddah (SA); Khalid M. El-Say, Jeddah (SA); Osama A. A. Ahmed, Jeddah (SA); Bader M. Aljaeid, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/691,678

(22) Filed: Nov. 22, 2019

(51) Int. Cl.
*A61K 9/107* (2006.01)
*A61K 31/4375* (2006.01)
*A61K 47/10* (2017.01)
*A61K 47/22* (2006.01)
*A61K 9/00* (2006.01)

(52) U.S. Cl.
CPC .......... *A61K 9/1075* (2013.01); *A61K 9/0043* (2013.01); *A61K 31/4375* (2013.01); *A61K 47/10* (2013.01); *A61K 47/22* (2013.01)

(58) Field of Classification Search
CPC .... A61K 9/1075; A61K 9/0043; A61K 47/22; A61K 47/10; A61K 31/4375
See application file for complete search history.

(56) References Cited

U.S. PATENT DOCUMENTS

| | | |
|---|---|---|
| 6,193,985 B1 | 2/2001 | Sonne |
| 2013/0345185 A1 | 12/2013 | Mitra et al. |
| 2016/0081976 A1* | 3/2016 | Bromley ............. A61K 31/355 424/456 |

OTHER PUBLICATIONS

Guo et al., European J. Pharma. Sciences 29 (2013) 175-186. (Year: 2013).*
Huang et al., "Technical study of vinpocetine micelles prepared by thin-film hydration method", Zhong Yao Cai, Nov. 2012; 35(11):1850-4.
Kouchak, "In Situ Gelling Systems for Drug Delivery", Jundishapur J Nat Pharm Prod. Aug. 2014; 9(3): e20126.
Nasr et al., "Neuroprotective effects of novel nanosystems simultaneously loaded with vinpocetine and piracetam after intranasal administration", Life Sci. Jun. 1, 2019;226:117-129.
Yang et al., "Recent Advances in the Application of Vitamin E TPGS for Drug Delivery", Theranostics 2018, 8(2): 464-485.
Zaki et al., "Enhanced bioavailability of metoclopramide HCl by intranasal administration of a mucoadhesive in situ gel with modulated rheological and mucociliary transport properties", Eur J Pharm Sci. Dec. 2007;32(4-5):296-307.

* cited by examiner

*Primary Examiner* — Robert S Cabral
(74) *Attorney, Agent, or Firm* — W&C IP

(57) ABSTRACT

Methods of enhancing cognition and/or memory and methods of treating cognitive and cerebrovascular disorders by intranasally administering an in situ gelling composition comprising micelles formed with tocopherol or a derivative thereof are provided. The micelles encapsulate a biological active agent such as vinpocetine. The methods provide for enhanced brain targeting of the biological active agent.

14 Claims, 5 Drawing Sheets

IN SITU GELLING COMPOSITION CONTAINING TOCOPHEROL-LOADED MICELLES AS AN INTRANASAL DRUG DELIVERY SYSTEM

FIELD OF THE INVENTION

The invention is generally related to the intranasal administration of an in situ gelling composition containing micelles formed from tocopherol to enhance the delivery of biological active agents such as vinpocetine to the brain.

BACKGROUND OF THE INVENTION

Drug solubility has been a common limitation in the development of new drug formulations. This may not be surprising given that more than a third of the drugs listed in the United States Pharmacopoeia are either poorly soluble or insoluble in water. Intranasal (IN) administration may achieve an effective therapeutic brain drug concentration, through the nose-brain pathway, that allows direct delivery to the cerebrospinal fluid.[4,5] Therefore, the IN route can diminish drug distribution to non-targeted sites and decrease systemic adverse effects.[2,6,7] Despite these advantages, IN delivery suffers from some restrictions such as poor drug permeability from nasal mucosa, mucociliary clearance, low drug retention time and nasomucosal toxicity.[8,9] To overcome these restrictions, various colloidal drug nanocarriers (NCs) especially the lipid-based ones have been utilized to improve the drug permeability and absorption.[7,10,11] The rapid nasal mucociliary clearance, that results in low absorption and poor bioavailability, could be overcome by development of mucoadhesive in situ nasal gelling drug delivery systems that prolong the retention time and control the drug delivery via this route.[12] Such formulations were intended to help IN-drug delivery but, the clinical success of IN therapy is limited owing to the irritation of the nasal mucosa or to the frequent and high dose of the formulation required. Hence, further development of suitable lipid-based NCs to overcome these barriers is needed.

Vinpocetine (VNP), derived from the natural vinca alkaloid vincamine, is widely utilized as a vasodilator and a nootropic agent.[1,2] VNP is used for improving memory and cerebral metabolism in cerebrovascular and age-related memory disorders.[3,4] The extensive first pass drug metabolism and low aqueous solubility hinders the full utilization of VNP oral dose because of its low oral bioavailability.[5] Due to the bioavailability problems with oral delivery of VNP, alternative and effective formulations for VNP delivery are needed, particularly to enhance delivery to the brain.

SUMMARY OF THE INVENTION

An aspect of the disclosure provides an in situ gelling composition comprising micelles formed with tocopherol or a derivative thereof; vinpocetine encapsulated within the micelles; and a thermosensitive polymer, wherein the composition forms a gel phase when said composition comes into contact with a surface at a temperature at or above 25° C. In some embodiments, the tocopherol is D-α-Tocopherol polyethylene glycol 1000 succinate (TPGS). In some embodiments, the thermosensitive polymer is poloxamer 407 which has a concentration of 20-25% w/v. In some embodiments, the composition further comprises Carbopol® 940 at a concentration of 0.2-0.7% w/v.

Another aspect of the disclosure provides a method of enhancing cognition and/or memory in a subject in need thereof, comprising intranasally administering to the subject an in situ gelling composition as described herein.

Another aspect of the disclosure provides a method of treating a cognitive disorder in a subject in need thereof, comprising intranasally administering to the subject an in situ gelling composition as described herein. In some embodiments, the cognitive disorder is selected from the group consisting of dementia, Huntington's disease, Parkinson's disease, and Alzheimer's disease.

Another aspect of the disclosure provides a method of treating a cerebrovascular disorder in a subject in need thereof, comprising intranasally administering to the subject an in situ gelling composition as described herein. In some embodiments, the cerebrovascular disorder is selected from the group consisting of stroke, vertebral stenosis, intracranial stenosis, aneurysm, and a vascular malformation.

DETAILED DESCRIPTION

Figure 1A:
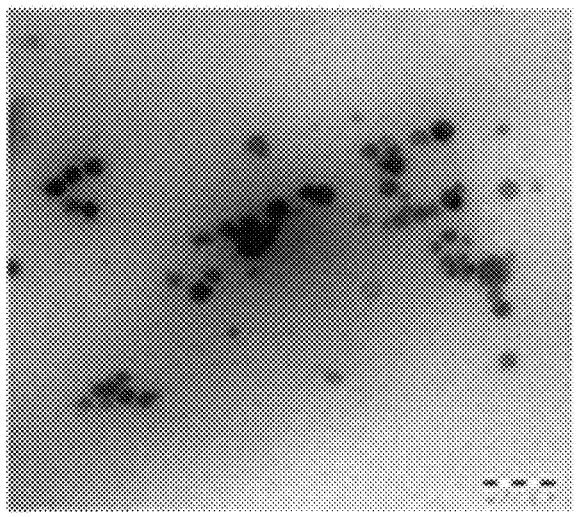
FIG. 1A-D. Transmission electron microscope images of the prepared lipid-based nanocarriers (A) SLN's, (B) TF's, (C) Peg-Lips, and (D) TPGS-micelles.
Figure 1B:
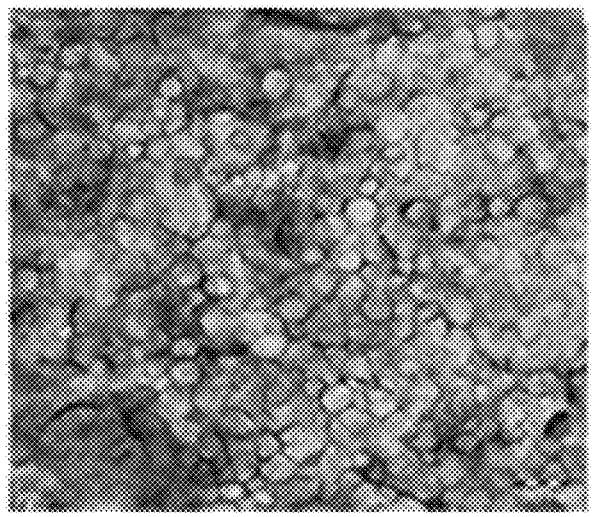
Figure 1C:
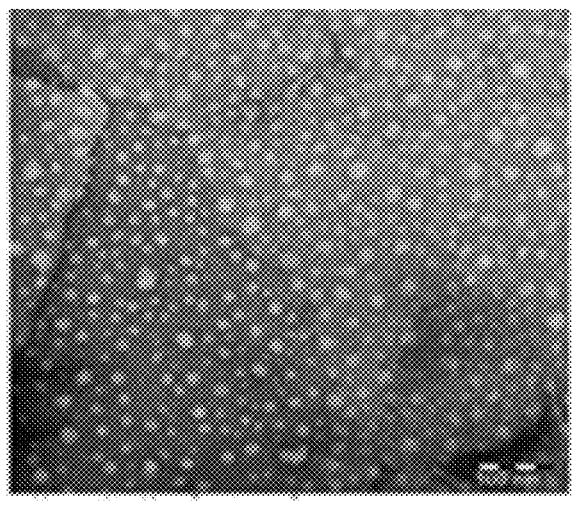
Figure 1D:
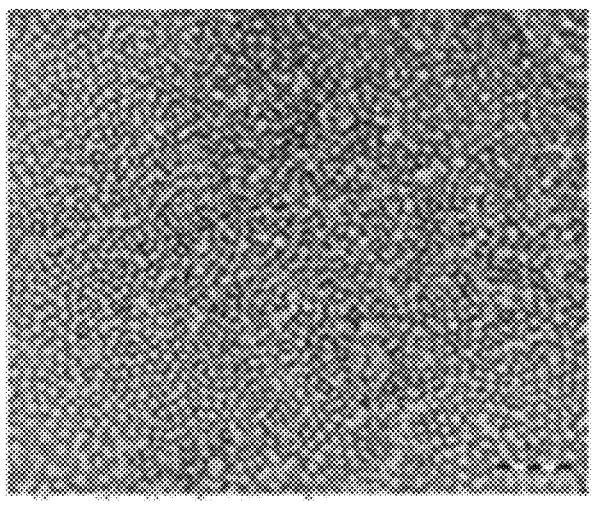

Embodiments of the disclosure provide thermosensitive in situ gelling systems comprising tocopherol containing micelles useful for the intranasal delivery of biological active agents such as VNP. The in situ gelling system according to embodiments of the disclosure enhances the delivery of active agents to the brain and is thus useful for improving treatment effectiveness of the delivered therapeutic agents.

As used herein, the term "micelle" refers to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a mixed micelle.

Polymeric micelles are exploited as pharmaceutical nanocarriers for the delivery of poorly water-soluble (i.e., water-insoluble) or hydrophobic drugs, which can be solubilized in the hydrophobic inner core of a micelle. Micelles can therefore serve to improve solubility and bioavailability of various hydrophobic drugs. The small size of micelles (typically about 10 to about 100 nm) allows for efficient accumulation of an associated active moiety into targeted tissues. Micelles can be formed from one or more polymeric nonionic surfactants.

Embodiments of the disclosure provide a tocopherol or derivative thereof as a nonionic surfactant. Tocopherols are a class of methylated phenols, many of which have vitamin E activity. Tocopherols and their derivatives, such as esters for example, are widely used in vitamin supplementation and as antioxidants in the food industry and in many pharmaceutical compositions. Tocopherols are a range of natural and synthetic compounds, also known by the generic term Vitamin E α-Tocopherol (chemical name: 2,5,7,8-tetramethyl-2-(4',8',12'-trimethyldecyl)-6-chromanole) is the most active and widely distributed in nature, and has been the most widely studied. Other members of the class include beta, gamma, and delta tocopherols. Tocopherols occur in a number of isomeric forms, the D and DL forms being the most widely available. As used herein, the term "tocopherol" includes all such natural and synthetic tocopherol or Vitamin E compounds.

Any of the forms or isomers of tocopherols and their derivatives, eg. esters may be used according to the present disclosure. Thus for example, α-tocopherol can be used as such or in the form of its esters such as α-tocopherol acetate, linoleate, nicotinate or hemi succinate-ester, many of which are available commercially.

The tocopherol derivative includes chemical derivatives of vitamin E with ester and ether linkages of various chemical moieties to polyethylene glycol of various lengths. For example, the derivative may include vitamin E tocopherol polyethylene glycol succinate (TPGS) derivatives with PEG molecular weights between about 500 and 6000 Da. In some embodiments, the vitamin E polymeric derivative is D-α-Tocopherol polyethylene glycol 1000 succinate (TPGS). In an embodiment, the TPGS is present in the composition from about 0.01 wt % to about 20 wt %/volume. It should be understood that throughout the specification the term weight percent (wt %) refers to mass per unit volume, unless otherwise specified.

TPGS is a water soluble derivative of Vitamin E in which polyethylene glycol subunits are attached by a succinic acid diester at the ring hydroxyl of the vitamin E molecule. TPGS is an almost odourless waxy amphiphilic substance with a molecular weight about 1513. TPGS forms stable micelles in aqueous vehicles for its amphiphilic structure with a hydrophile/lipophile balance (HLB) value of 13.2. TPGS has been approved as a pharmaceutical excipient by the United States Food and Drug Administration (FDA).[11]

The tocopherol surfactant of the disclosure may be used alone or in conjunction with other known surfactants eg. phospholipids, polysorbates, sorbitan esters of fatty acids, cetearyl glucoside or poloxamers or other stabilisers such as xanthan gum, or propylene glycol alginate. Preferably, the total amount of surfactants in the compositions of the presently disclosed embodiments is about 30 percent or less of the total composition with the remaining major component being water.

The present disclosure provides the use of a tocopherol or a derivative thereof for the preparation of a micelle composition for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is a central nervous system (CNS) acting drug characterized by poor bioavailability and limited brain concentration. In some embodiments, the active agent is VNP.

The micelle composition of the disclosure is preferably incorporated into an in situ gelling composition suitable for intranasal administration. There are various changes in conditions that can trigger the gelling of an in situ gelling composition. Among these are changes in pH, osmolality, temperature, water concentration, and alterations in specific ion concentrations.

Temperature-sensitive in situ gelling compositions generally change from a sol to a gel when the temperature exceeds a critical solution temperature, which in the case of drug delivery systems must be reasonably close to body temperature. An example is the polyethylene oxide-polypropylene oxide block copolymer, sold under the trade name Pluronic™ F 127. A 25-40% aqueous solution of this material will gel at about body temperature, and drug release from such a gel occurs over a period of up to one week. In some embodiments, the sol-gel transition temperature of the composition of the disclosure is at least 25° C., e.g. 25-35° C., e.g. 28-32° C., e.g. about 30° C.

A temperature-sensitive in situ gelling composition generally comprises a thermosensitive polymer such as poloxamers, gellan gum, alginic acid, xyloglucan, pectin, chitosan, poly(DL-lactic acid), poly(DL-lactide-co-glycolide) and poly-caprolactone. The choice of solvents like water, dimethylsulphoxide, N-methyl pyrrolidone, triacetin and 2-pyrrolidone for these formulations depends on the solubility of polymer used.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamers are also known by the trade names Synperonic®, Pluronic®, and Kolliphor®. Because the lengths of the polymer blocks can be customized, many different poloxamers exist that have slightly different properties. For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g. P407=poloxamer with a polyoxypropylene molecular mass of 4000 g/mol and a 70% polyoxyethylene content). In some embodiments, the thermosensitive polymer is poloxamer 407. In some embodiments, the concentration of thermosensitive polymer in the composition is 20-25% w/v, e.g. about 22% w/v.

The composition of the disclosure may further comprise a hydrophilic polymer such as polyacrylic acid (also known as Carbopol® or carbomer), chitosan, and hydroxypropyl methylcellulose to enforce the mechanical strength and overcome the possibility of the gel erosion. The IUPAC name of polyacrylic acid is poly(1-carboxyethylene). Carbomers may be homopolymers of acrylic acid, or crosslinked with an allyl ether of pentaerythritol, allyl ether of sucrose, or allyl ether of propylene. In a water solution at neutral pH, polyacrylic acid is an anionic polymer, i.e. many of the side chains of polyacrylic acid will lose their protons and acquire a negative charge. This makes polyacrylic acids polyelectrolytes, with the ability to absorb and retain water and swell to many times their original volume. Carbomer codes (910, 934, 940, 941, and 934P) are an indication of molecular weight and the specific components of the polymer. In some embodiments, the hydrophilic polymer is Carbopol® 940, a crosslinked polyacrylic acid polymer. In some embodiments, the concentration of hydrophilic polymer in the composition is 0.2-0.7% w/v, e.g. about 0.5% w/v.

The present disclosure also provides a method of treatment of a human or non-human animal subject by delivery of a substantially insoluble or sparingly soluble biologically active agent, said method comprising administering to said subject a micelle composition or in situ gelling composition of the invention as hereinbefore defined.

The compositions of the present disclosure may also contain other components such as, but not limited to, antioxidants, additives, adjuvants, buffers, tonicity agents, bioadhesive polymers, and preservatives. In any of the compositions of this disclosure, the mixtures are preferably formulated at about pH 5 to about pH 8. This pH range may be achieved by the addition of buffers to the composition. This pH range ensures that no irritancy is expected from the formulations following application on the nasal mucosa. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The micellar compositions of the present disclosure are stable in buffered aqueous solution. That is, there is no adverse interaction between the buffer and any other component that would cause the compositions to be unstable.

An exemplary antioxidant which may be included in the composition of the disclosure includes α-Lipoic acid (ALA), also known as thioctic acid. ALA is a substance in the form of yellow crystals having the structural formula $C_8H_{14}O_2S_2$ and the molecular weight of 206.3. ALA is also present in the human body, and is contained in many foods such as broccoli and red meat. ALA is an antioxidant that protects membranes through recycling vitamin E ALA can function as a redox regulator and showed effects in various oxidative stress models as ischemia-reperfusion injury and diabetes. In addition to its use as an oxidative agent, ALA being included in the micelle compositions of the disclosure also provides for enhancement of cognitive functioning in patients. In some embodiments, the percentage of ALA in TPGS in the micelle compositions disclosed herein is 1-30%, e.g. 10-20%, e.g. about 16.62%.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight.

In an embodiment, a composition of the present disclosure includes at least one bioadhesive polymer. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

The compositions disclosed herein have the bioactive agent, e.g. VNP, incorporated and/or encapsulated in micelles which are dispersed in an aqueous medium or incorporated into an in situ gelling system.

Embodiments of the disclosure also include methods of preparing the micelle compositions disclosed herein. Various suitable methods are known in the art. In an embodiment, the present disclosure provides a method of preparing a micelle composition that includes mixing an active agent (e.g. VNP) with a tocopherol (e.g. TPGS) in ethanol to form an ethanolic solution. In an embodiment, the method provides for adding distilled water to the prepared solution. The ethanol may then be evaporated, e.g. using a rotary vacuum evaporator. The prepared dispersion may then be centrifuged and the residue lyophilized using a freeze dryer.

Other suitable solvents that can be used in preparing the micelle compositions of the present disclosure include short-chain alcohols, for example, methanol, n-propanol, isopropanol, and butanol, as well as, chloroform, acetone, methylene chloride, dimethyl dulfoxide, dimethyl formamide and propylene glycol.

Embodiments of the disclosure also provide methods of preparing in situ gelling systems. Such methods are known in the art. In an embodiment, the thermosensitive polymer (e.g. poloxamer 407) and hydrophilic polymer (e.g. Carbopol® 940) are added to an aqueous cold dispersion of the prepared micelles at 4° C. on a magnetic stirrer.

The compositions of the disclosure may be useful for the treatment of any disease or disorder that the included active agent is useful for treating. For example, if VNP is used, the composition or dosage form may be useful for the treatment of cerebrovascular disorders such as stroke, vertebral stenosis, intracranial stenosis, aneurysm, and a vascular malformation and cognitive disorders such as dementia, Huntington's disease, Parkinson's disease, and Alzheimer's disease. In some embodiments, the composition or dosage form may be used to enhance cognition and/or memory in a healthy subject not having a cerebrovascular or cognitive disorder. In some embodiments, the composition or dosage form is used for the treatment of circulatory disorders which may occur in smokers and diabetics.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. VNP) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Intranasal drug administration is characterized by enhanced bioavailability, especially for drugs that easily cross the mucous membranes, due to the enriched vascular supply in the nasal cavity. This route avoids the drug destruction either by gastrointestinal enzymes or by hepatic first-pass effect. Moreover, the rate of absorption and plasma concentration of intranasal administered drugs are comparable to intravenous administration and are usually better than subcutaneous or intramuscular routes.[1,2] It is a non-invasive, simple, convenient and safe route for all patients.[3] In addition, intranasal administration may achieve an effective therapeutic brain drug concentration, through the nose-brain pathway, that allows direct delivery to the cerebrospinal fluid.[4,5] Therefore, the intranasal route can diminish drug distribution to non-targeted sites and decreases systemic adverse effects.[2,6,7]

Whilst the beneficial effects of the disclosure are particularly apparent in intranasal delivery, the utility of the disclosure is not limited and compositions according to the invention may also used for oral, buccal, rectal, vaginal, ocular, intraperitoneal, and parenteral drug delivery.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Vinpocetine (VPN) is a synthetic derivative of the Vinca Minor alkaloids. The drug is characterized by a short half-life, limited water solubility and high hepatic first-pass effect. The objective was to develop different lipid-based nanocarriers (NCs) loaded into a thermosensitive in situ gelling (ISG) system to improve VPN bioavailability and brain targeting via intranasal delivery. Different lipid-based NCs were developed and characterized for vesicle size, zeta potential, VPN entrapment efficiency (EE) and morphological characterization using Transmission electron microscope (TEM). The prepared NCs were loaded into ISG formulations and characterized for their mucoadhesive properties. Ex-vivo permeation and histological study of the nasal mucosa were conducted. Pharmacokinetic and brain tissue distribution were investigated and compared to a marketed VPN product following administration of a single dose to rats. VPN-D-α-Tocopherol polyethylene glycol 1000 succinate (TPGS) micelles nano-formulation showed the smallest particle size, highest EE among the studied NCs. TEM images revealed almost spherical shape for all the prepared NCs. Among NCs studied, VPN-loaded TPGS micelles demonstrated the highest percent cumulative VPN ex-vivo permeation. All the prepared ISG formulations revealed the presence of mucoadhesive properties and showed no signs of inflammation or necrosis upon histological examination. Rats administered intranasal VPN-loaded TPGS-micelles ISG showed superior VPN concentration in the brain tissue and significant high relative bioavailability when compared to those that received raw VPN-loaded ISG and marketed drug oral tablets. Accordingly, VPN-loaded TPGS-micelles ISG formulation is a successful brain drug delivery system with enhanced bioavailability for drugs with poor bioavailability and those that are frequently administered.

Materials and Methods

Materials

Vinpocetine (VPN) was procured from Wuhan Trustchem Fine Chemical Co., Ltd. Wuhan (Hubei, China). Glyceryl monostearate (GMS) was gifted from Nikkol chemicals Co., Ltd (Tokyo, Japan). Hydrogenated phosphatidylcholine (PC) (95% hydrogenated phosphatidylcholine, 0.5% hydrogenated lyso-phophatidylcholine) was obtained as a kind gift from American Lecithin company (Oxford, Conn., USA). Stearic acid was procured from Fischer Scientific (Loughborough, UK). Dicetyl phosphate (DCP), cholesterol, ethanol and methanol were purchased from Fisher Scientific (Pittsburgh, Pa.). Poloxamer 407 was obtained from Xi'an Lyphar Biotech Co., Ltd (Xi'an, China). TWEEN® 80, SPAN® 80, Polyethylene glycol (PEG) 4000, chloroform and D-α-Tocopherol polyethylene glycol 1000 succinate (TPGS) were procured from Sigma-Aldrich (St. Louis, Mo.). Carbopol® 940, a crosslinked polyacrylic acid polymer, was obtained from Acros Organics (Morris Plains, N.J.).

Preparation of Different Vinpocetine-Loaded Lipid-Based Nanocarriers

Different optimized VPN-loaded lipid-based NCs namely; solid lipid nanoparticles (SLNs), transfersomes (TFs), PEGylated liposomes (Peg-Lips), and TPGS-micelles were prepared as described in our previously published work.[17,18,30-33] Table 1 illustrates the composition of the prepared lipid-based NCs.

TABLE 1

Composition and characterization of VPN-loaded lipid-based NCs

| Nanocarrier type | Composition | | PS | | | EE |
|---|---|---|---|---|---|---|
| | Ingredients | Level | (nm) | PDI | ZP (mV) | (%) |
| SLNs | GMS (%) | 5 | 386 ± 27 | 0.481 | −3.16 ± 1.45 | 89.01 |
| | Surfactant (%) | 1 | | | | |
| | Surfactant HLB | 11.1 | | | | |
| TFs | VPN: PC (Molar Ratio) | 1:4.8 | 590 ± 47 | 0.444 | 1.89 ± 1.01 | 97.34 |
| | PC: Surfactant (%) | 95:5 | | | | |
| | Surfactant HLB | 4.3 | | | | |
| Peg-Lips | Hydrogenated PC (%) | 1.5 | 205 ± 73 | 0.494 | −52.27 ± 0.80 | 59.05 |
| | Cholesterol (%) | 0.25 | | | | |
| | DCP (%) | 0.3 | | | | |
| | PEG 4000 (%) | 0.25 | | | | |
| TPGS-micelles | TPGS (%) | 2 | 13 ± 2 | 0.484 | −2.79 ± 0.35 | 100 |

Note:
All NCs contain the same concentration of VPN (0.25%). SPAN® and TWEEN® were used as non-ionic surfactant.
Abbreviations: SLNs; Solid lipid nanoparticles, PEG; Polyethylene glycol, GMS; Glyceryl monostearate, VPN; Vinpocetine, TPGS; D-α-Tocopherol polyethylene glycol 1000 succinate, PS; particle size, ZP; zeta potential, EE; Entrapment Efficiency, DCP; Dicetyl Phosphate; PC, phosphatidylcholine Preparation of VPN-Loaded Solid Lipid Nanoparticles Melt-emulsion ultrasonication and low temperature-solidification was the technique utilized to develop VPN-loaded SLNs.[34,35] Briefly, the specified amount of glyceryl monostearate was heated at 80° C. and 0.25% w/v of VPN (based on the total volume of the formulation) was solubilized in the lipid phase. An aqueous surfactant (TWEEN® 80, SPAN® 80 or both) solution (80° C.) was prepared, added to the melted lipid phase and the mixture was stirred at 1200 rpm for 15 minutes at 80° C. until a milky color emulsion was formed. The prepared primary emulsion was then ultrasonicated for 10 minutes using a Sonics VCX 750, Sonics & Materials INC. (CT, USA) until a uniform nanodispersion was formed. The colloidal dispersion was promptly cooled by immersing the container into ice-cold water while stirring on a magnetic stirrer for 15 minutes until a homogenous dispersion was obtained.[31]

Preparation of VPN-Loaded Transfersomes

Preparation of VPN-loaded TFs was achieved using a lipid film hydration technique,[36] with some modifications. The specified amount of VPN (250 mg), phosphatidylcholine (PC), and non-ionic surfactant, described in Table 1, were dissolved in methanol using an ultrasonic bath. The obtained dispersion was subjected to rotary evaporation under reduced pressure at 45° C. until complete formation of a thin film on the flask wall. This film was maintained overnight in a vacuum oven to confirm complete removal of organic solvent. Finally, the film was then hydrated with 100 mL phosphate buffered saline (pH=7.5) for about 2 h at 19.8° C.[18]

Preparation of VPN-Loaded PEGylated Liposomes

A thin-film hydration technique was utilized to develop VPN-loaded Peg-Lips as previously described[30] with slight modifications. The calculated amounts of VPN (250 mg), hydrogenated PC, cholesterol, DCP, and PEG 4000 were dissolved in 40 mL of methanol in chloroform mixture (40% v/v). Organic solvents were removed under vacuum using Buchi Rotavapor R-200; BÜCHI Labortechnik AG (Flawil, Switzerland) at 60° C. until a thin film was formed. Traces of the organic solvents were removed after the film was kept overnight in a vacuum oven at 30° C. Multilamellar PEGylated liposomes were assembled by hydrating the dried lipid film at 60° C. with 100 mL of isotonic buffer for about 10 minutes. Finally, VPN-loaded Peg-Lips vesicles were subjected to vesicle size reduction using a probe sonicator, Qsonica, LLC., Newtown, (CT, USA) for 30 seconds.[30]

Preparation of VPN-Loaded TPGS-Micelles

VPN-loaded TPGS-micelles were prepared by dissolving VPN (0.25% w/v) and TPGS (2% w/v) in 50 mL of ethanol over a magnetic stirrer for about 5 minutes. Distilled water (100 mL) was added to the prepared dispersion. Ethanol was completely removed using Buchi Rotavapor R-200; BÜCHI Labortechnik AG (Flawil, Switzerland). The obtained micellar dispersion was kept in a refrigerator at 4° C. until further characterization.[33]

NCs Characterization

Particle Size and Zeta Potential Determination

Malvern Zetasizer Nano ZSP, Malvern Panalytical Ltd (Grovewood Road, United Kingdom), that utilizes the dynamic light scattering with non-invasive backscatter (NIBS) optics technique was used to determine the particle size and zeta potential of the prepared lipid based NCs. Measurement for each sample was done in triplicate.

Entrapment Efficiency Determination

For VPN-loaded SLNs, TFs, and Peg-Lips; the percent entrapment efficiency (EE) was determined using indirect centrifugation method. To isolate the free unentrapped VPN from the prepared NCs, aliquots from each formulation were centrifuged at 20,000 rpm for 1 hour at 4° C. The supernatant was collected and passed through 0.2 μm filter. VPN concentration was determined using a reported high-performance liquid chromatography (HPLC) method,[37] except for slight modifications. Briefly, the mobile phase was consisting of methanol and 0.05 ammonium acetate buffer mixture of pH 5.5 (80:20 v/v). The mobile phase was flowing at a rate of 1 mL/min through a Ponapak C18 analytical column, 4.6×250 I.D. mm, particle size 125A (Waters Associates, Ireland). The injection volume was adjusted at 20 μL and the detection wave length was set at 273 nm. The % VPN entrapped in each NCs formulation was calculated using equation 1.

$$EE(\%) = \frac{\text{Initial amount of } VPN \text{ used } - \text{Amount of unentrapped } VPN \text{ in the supernatant}}{\text{The initial amount of } VPN \text{ used}} \times 100 \quad \text{(Eq. 1)}$$

For VPN-loaded TPGS-micelles; the prepared micellar dispersion was centrifuged at 20000 rpm for 5 minutes at 4° C. to separate unloaded VPN.[38] The supernatant, which contained VPN-loaded TPGS-micelles, was collected, diluted with anhydrous ethanol and the drug concentration was determined using the HPLC method described above. The EE % was calculated using equation 2.

$$EE(\%) \text{ in micelles} = \frac{\text{The weight of } VPN \text{ in the micellar dispersion}}{\text{The weight of feeding } VPN} \times 100 \quad \text{(Eq. 2)}$$

Examination Using Transmission Electron Microscope

Few drops of each NCs formulation were mounted on a carbon-coated grid and left for approximately 2 minutes before examination using transmission electron microscope (TEM) Model JEM-1230, JOEL (Tokyo, Japan).

Incorporation of VPN-Loaded NCs into Thermosensitive ISG

ISG formulations loaded with NCs containing VPN equivalent to 0.25% w/v were developed using a combination of poloxamer 407 (22% w/v) and Carbopol® 940 (0.5% w/v) by cold method. Selection of poloxamer and Carbopol® levels was based on the polymeric concentrations that achieve good ISG formulation characterization, which are in good agreement with our previously published work.[31] Briefly, the calculated amount of poloxamer and Carbopol® were successively added to aqueous cold dispersion of VPN-loaded NCs at 4° C. on a magnetic stirrer. The obtained dispersions were kept in the refrigerator (6° C.) overnight. An ISG formulation loaded with raw VPN (0.25% w/v) was also prepared, using the same method described above.

Characterization of VPN-Loaded ISG Formulations

Gelation Temperature Determination

The sol-gel temperature ($T_{sol\text{-}gel}$) for the prepared ISG formulations was evaluated by the tube inversion method previously published.[39,40] Briefly, one milliliter of each formulation was placed in a glass vial and stored overnight in the fridge. Each ISG formulation was heated, with 1° C. increments per step, in a thermostatic control heating water bath. The $T_{sol\text{-}gel}$ was recorded in the temperature range 20-30° C. The $T_{sol\text{-}gel}$ was considered as the temperature at which the ISG solution stopped flowing after complete inversion of the tube.

Determination of the pH

The pH of the prepared ISG formulations was determined using a calibrated pH meter using pH/mV/° C. meter pH 11 series OAKTON®, manufactured by Euteoh Instruments (Thermo Fisher Scientific, Singapore). Determinations were carried out in triplicate.

Evaluation of the Mucoadhesive Strength

The mucin particle method was utilized to study the mucoadhesiveness of the ISG formulations.[31,41] Briefly, a bovine mucin suspension was prepared by dispersing a known weight (10 mg) of the mucin powder in 100 mL phosphate buffer solution of pH 7.4. Then, a specified weight (150 mg) of the ISG formulation was added to 10 mL of the prepared mucin suspension with continuous shaking. After incubation for 48 h, zeta potential of each mixture was estimated using a Malvern Zetasizer Nano ZSP, Malvern Panalytical Ltd (Grovewood Road, United Kingdom) and the obtained value was compared to that of the raw bovine mucin suspension. The mucoadhesiveness, interaction of the studied formulation components with mucin, was determined by identifying the change in zeta potential value.[31,41]

Ex Vivo Permeation Studies

The permeation of VPN, from the prepared ISG formulations loaded with either VPN-NCs or raw VPN, through excised bovine nasal mucosa was carried out using Franz diffusion cells, Microette Plus, Hanson research (CA, USA). Fresh nasal mucosa was carefully excised from the nasal cavity of a bovine snout that was obtained from a local slaughter house. The prepared nasal mucosal samples were placed in the diffusion apparatus. The donor compartment was filled with 250 μL of the ISG formulation. Cells of the receptor compartments were filled with 7 mL phosphate buffer of pH 6.8. The temperature was kept at 34° C. and stirring speed was adjusted at 400 rpm. Aliquots were automatically collected from the receptor media for 12 h at specified time intervals and replaced with fresh media. The concentration of VPN was determined using HPLC method described above. The experiment was performed in triplicate.

The permeation profiles of VPN were constructed by plotting the cumulative VPN amount permeated (Q) per unit area as a function of time. The steady-state flux ($J_{SS}$) was calculated for both the initial and the delayed permeation phases from the corresponding slopes. The permeability coefficients ($P_c$) were calculated by dividing the delayed flux by the initial drug load ($C_o$). The diffusivity (D) was also obtained by plotting the cumulative amount of VPN permeated versus the square root of time and applying equation 3.

$$D = \left(\frac{\text{Slope}}{2C_0}\right)^2 \times \pi \quad \text{(Eq. 3)}$$

Histological Examination of Nasal Mucosa

To explore any change or modification in the intra-nasal tissues that arises due to IN application of the VPN-loaded TPGS-micelle ISG formulation, microscopic examination of the treated nasal epithelium was accomplished. The studied ISG formulation was applied on freshly separated excised bovine nasal mucosa for 12 hours in the Franz diffusion cells as previously stated in the ex-vivo permeation study. Following treatment, nasal mucosal samples were removed and stored in formalin (10%), dehydrated and finally embedded in paraffin wax. Samples were cut into four-micron sections, stained with hematoxylin and eosin and Gomori's Trichrome and examined using Nikon Eclipse 80i digital imaging light microscopy (Kanagawa, Japan). For comparative study, control sample was also investigated. Each tissue sample was assessed for any sign of irritation, inflammation, and the appearance of epithelial and goblet cells.[42]

Pharmacokinetic and Brain Tissue Distribution after Intranasal Administration

The pharmacokinetics and brain tissue distribution of VPN following IN administration of ISG formulations containing either VPN-loaded TPGS-micelles or raw VPN was evaluated. The study was conducted in comparison with a marketed oral VPN tablet, VINPORAL® 5 mg (Amriya Pharmaceutical Industries Company, Alexandria, Egypt), to determine the relative bioavailability. The concentration of VPN in the brain was calculated using equation 4.

$$\text{VPN concentration (ng/g)} = \frac{\text{VPN concentartion in 1 ml homogenate} \times \text{Total volume of homogenate}}{\text{Average weight of rat brain}} \quad \text{(Eq. 4)}$$

Animal Population

Male Sprague-Dawley rats, with an average weight of 260 g, were kept in a pathogen-free space in the Department of Pharmacology and Toxicology, Faculty of Pharmacy, King Abdulaziz University (KAU), Jeddah, KSA. The animal experimental protocol was revised and approved by the Animal Ethics and Animal Care Committee, Faculty of Pharmacy, KAU (Approval No. 1031439). The study fulfilled with the Declaration of Helsinki, the Guiding Principle in Care and Use of Animals (DHEW production NIH 80±23), and the "Standards of Laboratory Animal Care" (NIH distribution #85±23, reconsidered in 1985). Rats were divided into three groups (15 per group). Group I; administered intranasal ISG formulation loaded with VPN-TPGS micelles, group II; given intranasal ISG formulation containing raw VPN, while group III administered oral marketed VPN tablet that was crushed and suspended in 0.25% sodium carboxymethyl cellulose solution. Each rat was administered a VPN dose of 10 mg/kg.

Sample Collection

Animals were anesthetized and blood samples of 0.5 mL (n=6) were taken at different time points of 0.5, 1, 1.5, 2, 4, 6, 8, 12 and 24 h. For brain tissue samples, animals were euthanized by cervical dislocation, brain tissues (n=3) were harvested after 6, 12 and 24 h and stored at −80° C. Brain tissues were homogenized in PBS. Plasma and brain tissue homogenate samples were treated and analyzed as described in the following section.

Chromatographic Quantification of VPN

The concentration of VPN in the plasma and brain tissue samples was analyzed by liquid chromatography-tandem mass spectrometry (LC-MS)/MS method. HPLC Agilent 1200 system equipped with Agilent 6420, triple quad mass spectrometer and controlled by Mass Hunter software was used. The separation was performed on a Nacherey Nagel, Nucleodur C18 column, 5 μm, 4.6×250 mm (Duren, Germany). The mobile phase comprised of 0.1% formic acid and acetonitrile (29:71, v/v) and the flow rate was adjusted at 0.5 ml/min VPN and the internal standard (IS) Valsartan were detected in a Single Ion Monitoring (SIM) scan mode with positive ion detection. The ions used for the SIM detection were m/z 351.1 for VPN, and m/z 436.1 for Valsartan.

Linearity and Recoveries

Linearity of the assay method within a VPN concentration range of 200-800 pg/μl was verified with a regression coefficient ($R^2$=0.9991). All the obtained results were within the acceptable criteria as previously stated in the recommended guidelines. The mean recovery of VPN was 102.2% at 200 pg/μl (LLOQ) and 97.5% at 800 pg/μl (ULOQ).

Sample Extraction Procedure

To a 200 μL of the plasma sample or brain tissue homogenate, 50 μL of Valsartan (IS) and 1 mL of acetonitrile were added. The resulting solution was thoroughly vortex-mixed for 10 s. After centrifugation at 5000 rpm for 5 min, 5 μL of the supernatant was injected into the HPLC system for analysis. Concentration of VPN in the unknown samples was calculated from the regression equation obtained from the constructed calibration curve.

Pharmacokinetic Treatment

The pharmacokinetic parameters of VPN in the collected plasma data were assessed using non-compartmental pharmacokinetic treatment utilizing Kinetica™ software (version 4, Thermo Scientific, MA, USA). The maximum plasma VPN concentration ($C_{max}$), time to reach maximum VPN plasma concentration ($t_{max}$), area under the plasma VPN concentration time curve from zero to the last measurable VPN concentration ($AUC_{0-t}$), area under the plasma VPN concentration time curve from zero to infinity ($AUC_{0-\alpha}$), mean residence time (MRT), the elimination rate constant, elimination half-life, and total body clearance were measured. The data were expressed as the mean±standard deviation.

Statistical Analysis of the Data

The data obtained was analyzed using GraphPad Prism 6 (GraphPad Software, San Diego, Calif.) software. Two-way analysis of variance (ANOVA) followed by Tukey's multiple comparisons test was used to assess the significance of the difference between the investigated groups.

Results and Discussion

Evaluation of the Prepared Vinpocetine-Loaded Lipid-Based Nanocarriers

Table 1 shows the results of the particle size for the prepared NCs formulations. VPN-loaded TFs revealed the largest size (590±47 nm), while VPN-loaded TPGS-Micelles displayed the smallest size (13±2 nm). Furthermore, the polydispersity index of the prepared VPN-loaded lipid-based NCs was between 0.444-0.494, which indicates acceptable size distribution. TEM images (FIG. 1) showed a spherical particle morphology for all the prepared colloidal dispersions. The obtained images confirmed the uniformity in size distribution that were comparable with the data obtained by the Zetasizer Nano ZSP. Due to its content of the charge inducing agent (DCP), the colloidal dispersion of VPN-loaded Peg-Lips showed the highest stability with a zeta potential value of −52.27±0.80 mV. This Peg-Lips displayed the lowest percentage of VPN entrapped (59.05%), whereas the remaining NCs formulations exhibited high VPN EE that ranged from 89.01 to 100%. TPGS-micelles demonstrated the highest EE of about 100% which could be attributed to the nature of the drug loaded. Yang et al, reported high drug encapsulation efficiency for TPGS based fabricated NCs.[43] Zhu et al also stated 85-95% EE for docetaxel vitamin E TPGS NPs.[44] Similarly, Muthu et al mentioned an encapsulation efficiency up to 84.30±0.80% for docetaxel-loaded vitamin E TPGS micelles.[45] The prepared transfersomes and SLNs formulations showed high drug entrapment of 97.01 and 89.34%, respectively. The PEGylated liposomes displayed the lowest drug EE of 59.05% which is in a good accordance with the previously reported EE results of the same formulation.[30]

Evaluation of the Prepared VPN-Loaded ISG Formulations

Poloxamer 407 (22% w/v) and Carbopol® 940 (0.5% w/v) combination was found to be the optimum concentration for the polymeric solution to form ISG formulations loaded with different NCs. Addition of hydrophilic polymer such as Carbopol® 940 to poloxamer 407 enforces the mechanical strength and overcomes the possibility of the gel erosion.[46]

The sol-gel transition temperature of the colloidal dispersions was ranged from 25.33±1.53° C. for TFs-ISG to 30.00±1.00° C. for TPGS-micelles-ISG. It has been previously reported that an ISG system with a sol-gel transition temperature higher than but close to 25° C. is anticipated to be highly viscous at room temperature, the favorable sol-gel transition temperature should be close to but not exceed 30° C.[47] In addition, the reported temperature in the human nose is ranged from 30.2±1.7° C. to 34.4±1.1° C.,[48-50] the sol-gel transition temperature of the prepared formulations ensures the suitability of their application on the nasal mucosa. Our results revealed that the pH of the formulations ranged from 5.54±0.02 to 7.06±0.02. This pH range indicated that no irritancy is expected from the formulations following application on the nasal mucosa. All the prepared ISG formulations revealed presence of mucoadhesive properties as indicated by the change in zeta potential value for all the studied ISG formulation when compared with raw bovine mucin suspension. The prepared mucin suspension showed a negative zeta potential value of −9.88 mv. This value is attributed to ionization of the mucin carboxyl groups as previously stated.[31] A marked decrease in the mucin zeta potential value was noticed upon mixing with the prepared ISG formulations. This finding is an indication of the formulation mucoadhesive properties brought about by interaction between mucin and the polymeric ISG formulation.

Ex Vivo Permeation Studies

Figure 2A:
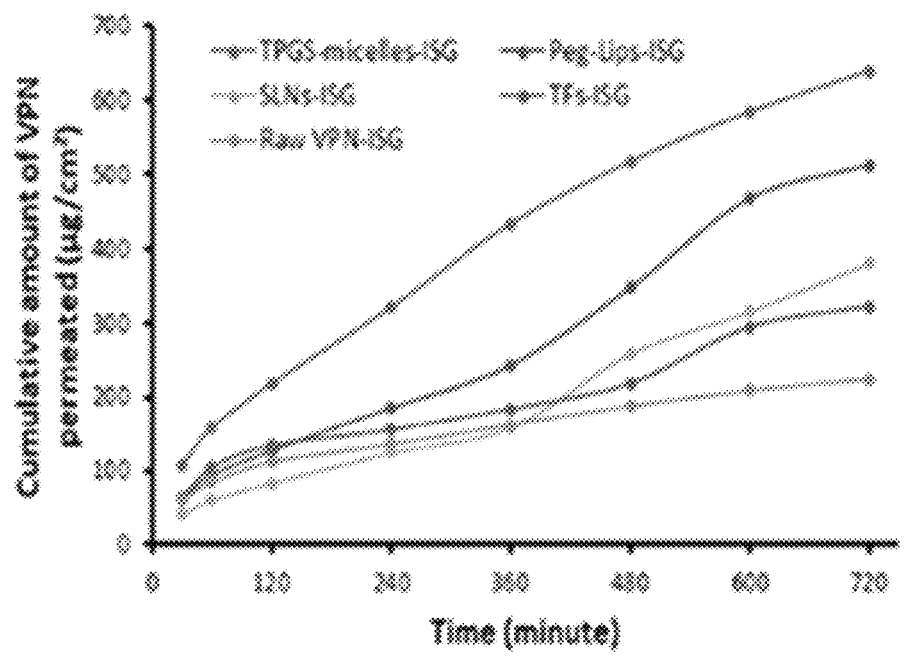
FIG. 2A-B. Cumulative amount of VPN permeated per unit area against time (A) and against square root of time (B) from different NCs loaded ISG formulations compared with the raw VPN-ISG.
Figure 2B:
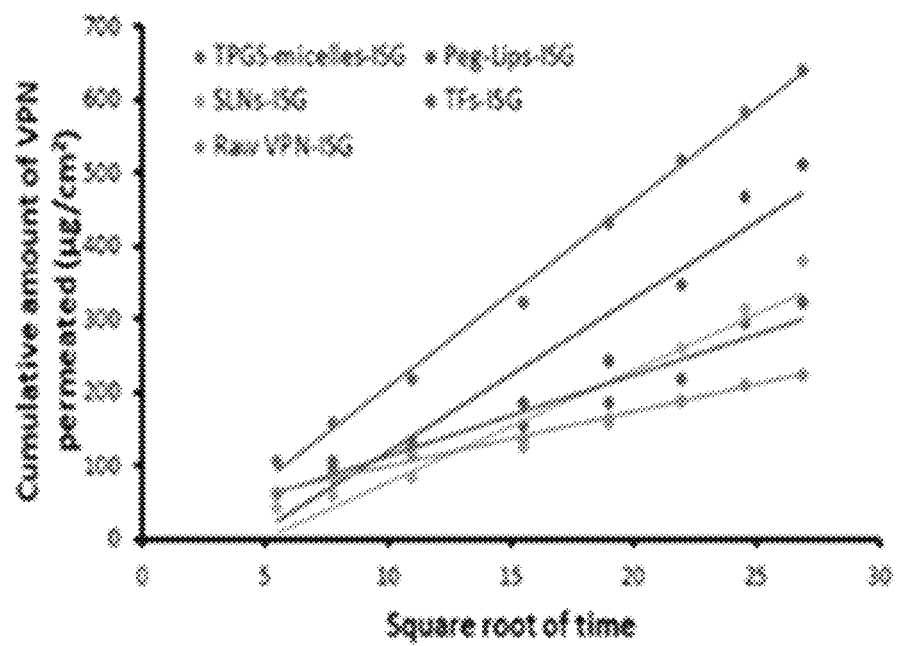

Table 2 showed the permeation parameters of VPN from different NCs-loaded ISG formulations compared with raw VPN-loaded ISG across bovine nasal mucosa. The permeation studies showed that higher permeability coefficient, diffusion coefficient and maximum amount of drug permeated ($D_{max}$) were noticed from VPN-loaded Peg-Lips-ISG followed by VPN-loaded TPGS-micelles-ISG which is an indication of the ability of these NCs to penetrate the nasal mucosa to a greater extent when compared with the other NCs-loaded ISG formulations and the raw VPN-loaded ISG. Also, the Peg-Lips-ISG and TPGS-micelles-ISG formulation recorded the highest steady state permeation fluxes (Jss) of 0.7913 and 0.7258 μg/cm².h, respectively. While their permeability coefficients (Kc) reaching 0.0012 and 0.0011 cm/h, respectively, indicating a general better permeation results than other NC formulations (FIG. 2). The highest amount of drug diffused (639.029 μg) with lowest percentage of VPN permeated over 12 h (58.38%) reflect the superiority of TPGS-micelles-ISG in the diffusivity and in sustaining the permeation over the other NCs formulations. The lipophilic nature and the small particle size of micelles could explain this nasal permeation enhancement. Another reason for this finding encompasses the fact that the formation of an occlusive monolayer film on a large surface area of the mucous membrane that diminishes the loss of moisture due to evaporation, which can enhance the drug permeation.[51] Additionally, the surfactant activity of TPGS can fluidize or loosen the intercellular lipid layer of the nasal mucosa and so enhances the drug permeation.[52,53] Also, the enhanced permeability of TPGS-micelles might be attributed to the P-glycoprotein (P-gp) inhibitory effects which has been 1E) approved by the FDA.[54-56]

TABLE 2

Gelation temperature and Ex vivo permeation parameters of VPN from different NCs-loaded ISG compared with raw VPN-loaded ISG across bovine nasal mucosa

| Formula | Gelation Temperature (° C.) | Cumulative VPN permeated (%) | $D_{max}$ (μg) | Steady State Flux ($J_{ss}$) (μg/cm².h) | Permeability Coefficient (Pc) (cm/h) | Diffusion Coefficient (D) |
|---|---|---|---|---|---|---|
| TPGS-micelles-ISG | 29.00 ± 1.73 | 58.38 ± 5.19 | 639.029 | 0.7258 | 0.001116626 | 0.001581934 |
| Peg-Lips- | 25.33 ± | 49.57 ± | 511.941 | 0.7913 | 0.001217435 | 0.001814617 |

TABLE 2-continued

Gelation temperature and Ex vivo permeation parameters of VPN from different NCs-loaded ISG compared with raw VPN-loaded ISG across bovine nasal mucosa

| Formula | Gelation Temperature (° C.) | Cumulative VPN permeated (%) | $D_{max}$ (μg) | Steady State Flux ($J_{ss}$) (μg/cm².h) | Permeability Coefficient (Pc) (cm/h) | Diffusion Coefficient (D) |
|---|---|---|---|---|---|---|
| ISG | | 1.53 | | 7.42 | | |
| SLNs-ISG | 26.67 ± 1.15 | 78.76 ± 4.19 | 379.501 | 0.5585 | 0.000859353 | 0.000911253 |
| TFs-ISG | 30.00 ± 1.00 | 98.31 ± 2.82 | 322.203 | 0.3771 | 0.000580095 | 0.000407787 |
| Raw VPN-ISG | 23.67 ± 0.58 | 34.54 ± 7.80 | 224.536 | 0.2039 | 0.000313735 | 0.000123760 |

Note:
0.5% CARBOPOL® 940 and 22% poloxamer 407 were used in each ISG formulation.

Figures 3A, 3B:
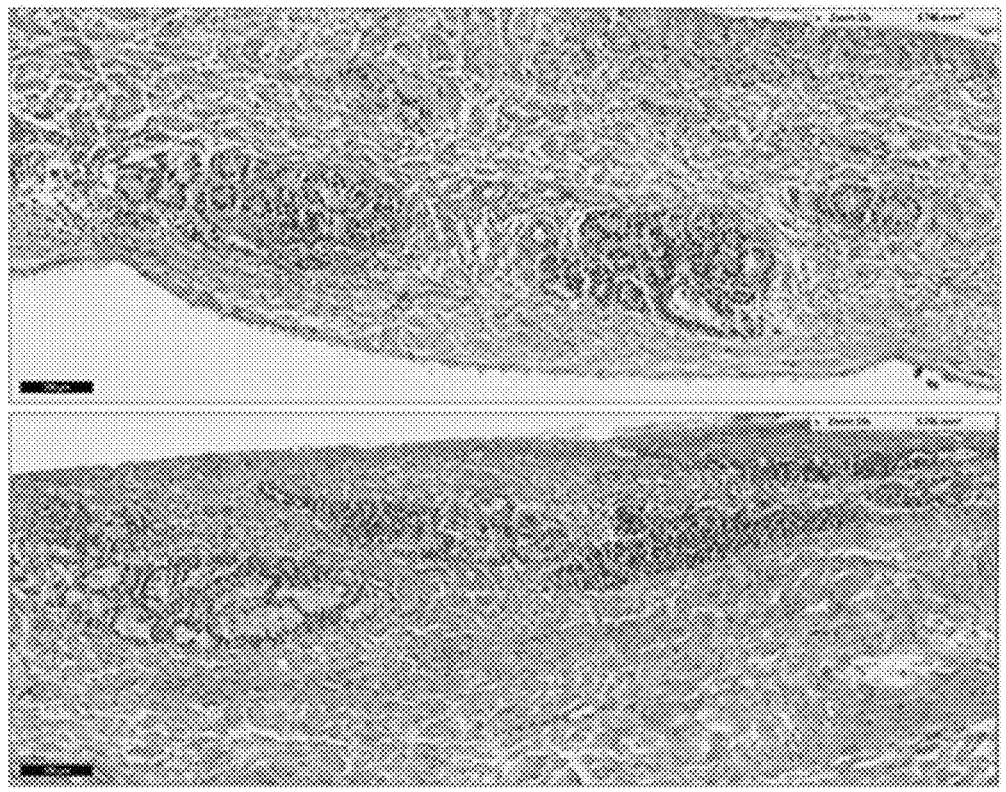
FIG. 3A-B. Histological images of the bovine nasal mucosa; (A) After 12 hrs treatment with VPN-loaded TPGS-micelle ISG; (B) The normal (untreated) nasal mucosa.

Assessment of Nasal Mucosa Irritancy Upon Application of TPGS-Micelles-ISG Formulation FIG. 3 demonstrates the histological photomicrographs of the nasal mucosa after 12 h of treatment with VPN-loaded TPGS-micelle ISG (A) and the normal (untreated) nasal mucosa (B). No signs of irritancy or inflammation have been observed on the treated nasal tissue. Also, normal appearance of both ciliated respiratory epithelium and goblet cells have been noticed. Therefore, the poloxamer-based ISG formulation is considered safe to use with respect to nasal administration which is in a good accordance with a previous study.[31]

Brain Tissue Distribution and Pharmacokinetics

Figure 4:
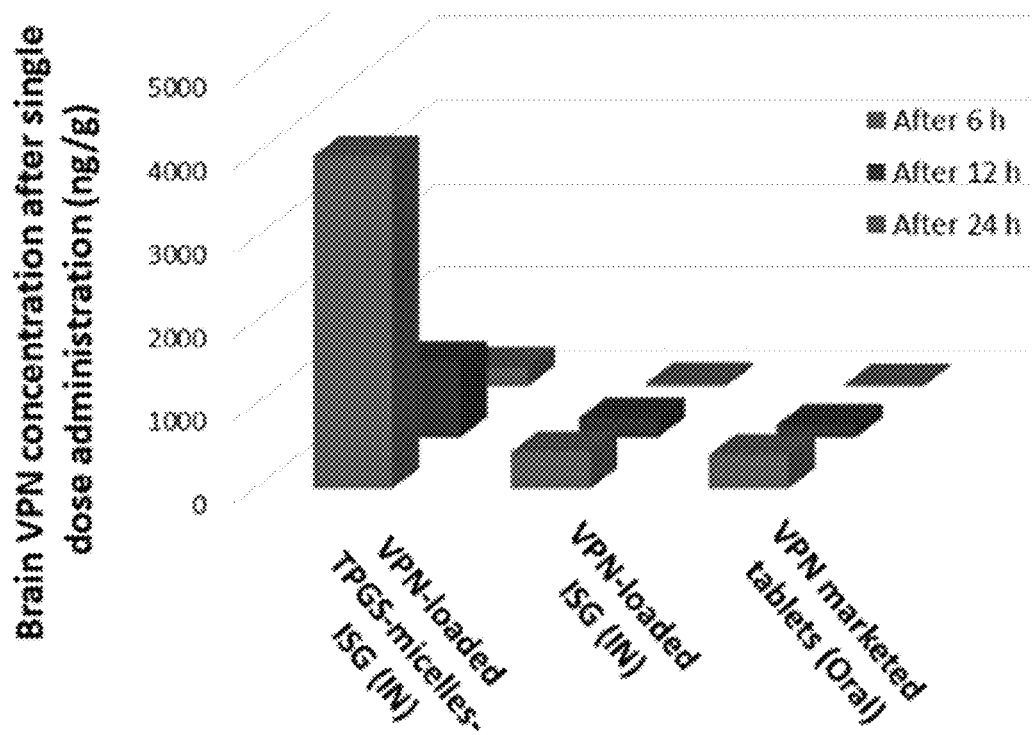
FIG. 4. Brain concentration of VPN in rats after intranasal administration of VPN-loaded TPGS-micelle ISG in comparison with raw VPN-loaded ISG and oral administration of the marketed VPN tablet (10 mg/kg) at different time points.
Figure 5:
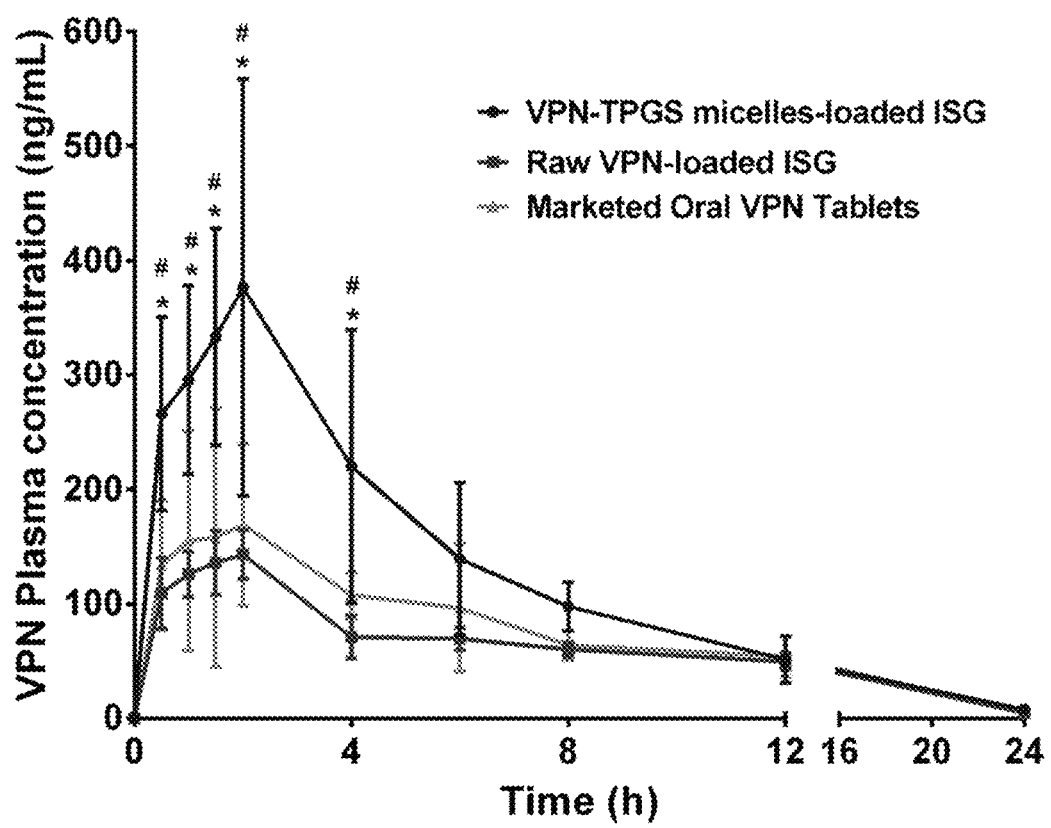
FIG. 5. Plasma concentration versus time profiles of VPN in rats after intranasal administration of VPN-loaded TPGS-micelle ISG in comparison with raw VPN-loaded ISG and oral administration of the marketed VPN tablet (10 mg/kg). Each point represents mean±S.D. (n=6). * and #: p<0.05 vs raw VPN-loaded ISG and marketed VPN tablet, respectively.

To evaluate the in vivo effectiveness of the developed VPN-loaded TPGS-micelles ISG formulation after IN administration to male Sprague Dawley rats, the brain distribution and the pharmacokinetics were studied and compared to raw VPN-loaded ISG formulation and a marketed oral VPN tablet. The concentration of VPN in the rat's brain tissue at different time points is shown in FIG. 4. The nasal administration of VPN-loaded TPGS-micelles ISG formulation exhibited approximately 10-fold higher in brain tissue than the corresponding raw VPN-loaded ISG formulation and the marketed oral VPN tablets after 6 hours. The plasma concentration versus time profiles after IN administration of VPN-loaded TPGS-micelles ISG and the raw VPN-loaded ISG as well as the oral administration of VPN tablet are shown in FIG. 5. The pharmacokinetic parameters for each group are summarized in Table 3. In the brain tissue, rats administered VPN-loaded TPGS-micelles ISG showed a much higher VPN concentration profile in comparison to those that received oral tablet which displayed irrelevant difference with rats administered raw VPN-loaded ISG (FIG. 4). It was reported that the human nasal respiratory and olfactory mucosa contain an efflux transporter known as P-glycoprotein which plays an important role in actively preventing the drug's influx from the nasal membrane.[57,58] Therefore, the incorporation of P-gp inhibitor as TPGS in the micelles could influence the penetration of the blood-brain barrier (BBB) and enhance the brain uptake with higher concentrations after IN administration.[59] This finding indicates that development of VPN in the form of TPGS-micelles ISG played a major role in enhancement of the drug nasal absorption and results in enhanced drug brain circulation using the TPGS micelles.

TABLE 3

Pharmacokinetic parameters ± SD of VPN following the intranasal administration of a single dose (10 mg/kg) of VPN-loaded TPGS-micelles-ISG in comparison with the intranasal administration of raw VPN-loaded ISG and the oral administration of VPN tablet by rats

| Pharmacokinetic parameter | VPN oral tablet | VPN-loaded TPGS-Micelles-ISG | Raw VPN-loaded ISG |
|---|---|---|---|
| $C_{max}$ (ng/mL) | 169.064 | 376.495* | 143.168 |
| $t_{max}$ (h) | 2.0 | 2.0 | 2.0 |
| $AUC_{(0-24)}$ (ng · h/mL) | 1498.34 ± 9.12 | 2388.568 ± 10.32* | 1253.638 ± 7.54 |
| $AUC_{(24-\infty)}$ (ng · h/mL) | 32.13695 ± 0.72 | 47.694 ± 0.15 | 33.739 ± 0.94 |
| $AUC_{(0-\infty)}$ (ng · h/mL) | 1530.477 ± 7.18 | 2436.262 ± 34.34* | 1287.377 ± 10.18 |
| $AUMC_{(0-24)}$ ng · hr²/mL | 10129.395 | 13248.332 | 8858.649 |
| $AUMC_{(24-end)}$ ng · hr²/mL | 771.287 | 572.325 | 809.737 |
| $AUMC_{(0-end)}$ ng · hr²/mL | 10900.681 | 13820.657 | 9668.386 |
| $K_{el}$ (h$^{-1}$) | 0.156 | 0.164 | 0.141 |
| $t_{1/2}$ (h) | 4.454 | 4.237 | 4.922 |
| MRT (h) | 7.122 | 5.673 | 7.510 |
| Relative bioavailability (%) | 100.0 | 159.183 | 84.116 |

Notes:
*significant difference at P < 0.05 (unpaired t test).
Abbreviations: VPN, Vinpocetine; ISG, in situ gel; AUC, area under the time-concentration curve; $C_{max}$, maximum plasma concentration; $K_{el}$, elimination rate constant; MRT, mean residence time; $t_{max}$, time to reach $C_{max}$.

Finally, the developed thermosensitive ISG loaded with TPGS micelles exhibited enhancement in the pharmacokinetic parameters with significant high relative bioavailability. VPN-loaded TPGS-micelles ISG showed a significant increase in VPN $C_{max}$ by 2.2- and 2.6-fold when compared with the oral VPN tablet and the raw VPN-loaded ISG, respectively. All formulations reached the maximum plasma concentration after 2 hours with no significant difference in the elimination half-life (P-value >0.05). The relative bioavailability of VPN from TPGS-micelles ISG was 159.183% compared with the oral marketed tablet. Whereas, the bioavailability of VPN was reduced to 84.116% after IN administration of the raw VPN-loaded ISG when compared with the marketed tablet. This finding confirms the superiority of TPGS-micelles in the brain delivery of VPN via administration of thermosensitive IN ISG.

CONCLUSION

Successful development of VPN-loaded TPGS-micelles ISG formulation is a key solution for VPN short half-life and poor bioavailability. Moreover, the prepared formulation enhanced the drug brain delivery and was superior to the marketed drug oral product. Therefore, this formulation represents a good alternative for currently available marketed drug product.

REFERENCES

1. Henry R, Ruano N, Casto D, Wolf R. A pharmacokinetic study of midazolam in dogs: nasal drop vs. atomizer administration. *Pediatr Dent.* 1998; 20(5):321-326.
2. Pires P C, Santos A O. Nanosystems in nose-to-brain drug delivery: A review of non-clinical brain targeting studies. *J Control Release.* 2018; 270:89-100. doi:10.1016/J.J-CONREL.2017.11.047.
3. Dhuria S V., Hanson L R, Frey W H. Intranasal delivery to the central nervous system: Mechanisms and experimental considerations. *J Pharm Sci.* 2010; 99(4):1654-1673. doi:10.1002/jps.21924.
4. Agrawal M, Saraf S, Saraf S, et al. Nose-to-brain drug delivery: An update on clinical challenges and progress towards approval of anti-Alzheimer drugs. *J Control Release.* 2018; 281:139-177. doi:10.1016/j.j-conrel.2018.05.011.
5. Liu Z, Jiang M, Kang T, et al. Lactoferrin-modified PEG-co-PCL nanoparticles for enhanced brain delivery of NAP peptide following intranasal administration. *Biomaterials.* 2013; 34(15):3870-3881. doi:10.1016/j.biomaterials.2013.02.003.
6. El-Zaafarany G M, Soliman M E, Mansour S, Awad G A S. Identifying lipidic emulsomes for improved oxcarbazepine brain targeting: In vitro and rat in vivo studies. *Int J Pharm.* 2016; 503(1-2):127-140. doi:10.1016/j.ijpharm.2016.02.038.
7. Salama H A, Mahmoud A A, Kamel A O, Abdel Hady M, Awad G A S. Phospholipid based colloidal poloxamer-nanocubic vesicles for brain targeting via the nasal route. *Colloids Surfaces B Biointerfaces.* 2012; 100:146-154. doi:10.1016/j.colsurfb.2012.05.010.
8. Illum L. Transport of drugs from the nasal cavity to the central nervous system. *Eur J Pharm Sci.* 2000; 11(1):1-18. doi:10.1016/50928-0987(00)00087-7.
9. Minn A, Leclerc S, Heydel J M, et al. Drug transport into the mammalian brain: The nasal pathway and its specific metabolic barrier. *J Drug Target.* 2002; 10(4):285-296. doi:10.1080/713714452.
10. Lockman P R, Mumper R J, Khan M A, Allen D D. Nanoparticle technology for drug delivery across the blood-brain barrier. *Drug Dev Ind Pharm.* 2002; 28(1):1-13. doi:10.1081/DDC-120001481.
11. Feng Y, He H, Li F, Lu Y, Qi J, Wu W. An update on the role of nanovehicles in nose-to-brain drug delivery. *Drug Discov Today.* 2018; 23(5):1079-1088. doi:10.1016/J.DRUDIS.2018.01.005.
12. Ugwoke M I, Verbeke N, Kinget R. The biopharmaceutical aspects of nasal mucoadhesive drug delivery. *J Pharm Pharmacol.* 2001; 53(1):3-22. doi:10.1211/0022357011775145.
13. Davis M E, Chen Z, Shin D M. Nanoparticle therapeutics: an emerging treatment modality for cancer. *Nat Rev Drug Discov.* 2008; 7(9):771-782. doi:10.1038/nrd2614.
14. Fenske D B, Cullis P R. Liposomal nanomedicines. *Expert Opin Drug Deliv.* 2008; 5(1):25-44. doi:10.1517/17425247.5.1.25.
15. Puri A, Loomis K, Smith B, et al. Lipid-based nanoparticles as pharmaceutical drug carriers: from concepts to clinic. *Crit Rev Ther Drug Carrier Syst.* 2009; 26(6):523-580. http://www.ncbi.nlm nih.gov/pubmed/20402623. Accessed Oct. 10, 2018.
16. Ahmed T A, El-Say K M, Aljaeid B M, Fahmy U A, Abd-Allah F I. Transdermal glimepiride delivery system based on optimized ethosomal nano-vesicles: Preparation, characterization, in vitro, ex vivo and clinical evaluation. *Int J Pharm.* 2016; 500(1-2):245-254. doi:10.1016/j.ijpharm.2016.01.017.
17. Badr-Eldin S M, Ahmed O A A. Optimized nano-transfersomal films for enhanced sildenafil citrate transdermal delivery: Ex vivo and in vivo evaluation. *Drug Des Devel Ther.* 2016; 10:1323-1333. doi:10.2147/DDDT.S103122.
18. Ahmed T A. Preparation of transfersomes encapsulating sildenafil aimed for transdermal drug delivery: Plackett-Burman design and characterization. *J Liposome Res.* 2015; 25(1):1-10. doi:10.3109/08982104.2014.950276.
19. Zhang X-G, Miao J, Dai Y-Q, Du Y-Z, Yuan H, Hu F-Q. Reversal activity of nanostructured lipid carriers loading cytotoxic drug in multi-drug resistant cancer cells. *Int J Pharm.* 2008; 361(1-2):239-244. doi:10.1016/j.ijpharm.2008.06.002.
20. Martins S, Sarmento B, Ferreira D C, Souto E B. Lipid-based colloidal carriers for peptide and protein delivery—liposomes versus lipid nanoparticles. *Int J Nanomedicine.* 2007; 2(4):595-607. http://www.ncbi.nlm nih.gov/pubmed/18203427. Accessed Oct. 10, 2018.
21. El-Say K M, Hosny K M. Optimization of carvedilol solid lipid nanoparticles: An approach to control the release and enhance the oral bioavailability on rabbits. Ahmad A, ed. *PLoS One.* 2018; 13(8):e0203405. doi:10.1371/JOURNAL.PONE.0203405.
22. Zhang Y, Huang Y, Li S. Polymeric micelles: nanocarriers for cancer-targeted drug delivery. *AAPS PharmSciTech.* 2014; 15(4):862-871. doi:10.1208/s12249-014-0113-z.
23. Varma M V S, Panchagnula R Enhanced oral paclitaxel absorption with vitamin E-TPGS: Effect on solubility and permeability in vitro, in situ and in vivo. *Eur J Pharm Sci.* 2005; 25(4-5):445-453. doi:10.1016/j.ejps.2005.04.003.
24. Zhang Z, Tan S, Feng S-S. Vitamin E TPGS as a molecular biomaterial for drug delivery. *Biomaterials.* 2012; 33(19):4889-4906. doi:10.1016/j.biomaterials.2012.03.046.
25. Tan S, Zou C, Zhang W, Yin M, Gao X, Tang Q. Recent developments in d-α-tocopheryl polyethylene glycol-succinate-based nanomedicine for cancer therapy. *Drug Deliv.* 2017; 24(1):1831-1842. doi:10.1080/10717544.2017.1406561.

26. Dintaman J M, Silverman J A. Inhibition of P-glycoprotein by D-alpha-tocopheryl polyethylene glycol 1000 succinate (TPGS). *Pharm Res.* 1999; 16(10):1550-1556. http://www.ncbi.nlm nih.gov/pubmed/10554096. Accessed Oct. 12, 2018.
27. Ogunrin A. Effect of vinpocetine (Cognitol™) on cognitive performances of a nigerian population. *Ann Med Health Sci Res.* 2014; 4(4):654-661. doi:10.4103/2141-9248.139368.
28. Luo Y, Chen D, Ren L, Zhao X, Qin J. Solid lipid nanoparticles for enhancing vinpocetine's oral bioavailability. *J Control Release.* 2006; 114:53-59. doi:10.1016/j.jconre1.2006.05.010.
29. Liu M, Zhang S, Cui S, et al. Preparation and evaluation of Vinpocetine self-emulsifying pH gradient release pellets. *Drug Deliv.* 2017; 24(1):1598-1604. doi:10.1080/10717544.2017.1388453.
30. Harbi I, Aljaeid B, El-Say K M, Zidan A S. Glycosylated Sertraline-Loaded Liposomes for Brain Targeting: QbD Study of Formulation Variabilities and Brain Transport. *AAPS PharmSciTech.* 2016; 17(6): 1404-1420. doi:10.1208/s12249-016-0481-7.
31. Ahmed T A, Badr-Eldin S M, Ahmed O A A, Aldawsari H. Intranasal optimized solid lipid nanoparticles loaded in situ gel for enhancing trans-mucosal delivery of simvastatin. *J Drug Deliv* Sci Technol. 2018; 48 (July):499-508. doi:10.1016/J.JDDST.2018.10.027.
32. Ahmed O A A, Badr-Eldin S M. In situ misemgel as a multifunctional dual-absorption platform for nasal delivery of raloxifene hydrochloride: formulation, characterization, and in vivo performance *Int J Nanomedicine.* 2018; Volume 13:6325-6335. doi:10.2147/IJN.S181587.
33. Ahmed O A A, El-Say K M, Aljaeid B M, Badr-Eldin S M, Ahmed T A. Optimized vinpocetine-loaded vitamin E D-α-tocopherol polyethylene glycol 1000 succinate-alpha lipoic acid micelles as a potential transdermal drug delivery system: in vitro and ex vivo studies. *Int J Nanomedicine.* 2019; 14:33-43.
34. Hao J, Wang X, Bi Y, et al. Fabrication of a composite system combining solid lipid nanoparticles and thermosensitive hydrogel for challenging ophthalmic drug delivery. *Colloids Surfaces B Biointerfaces.* 2014; 114:111-120. doi:10.1016/j.colsurfb.2013.09.059.
35. Silva A C, González-Mira E, García M L, et al. Preparation, characterization and biocompatibility studies on risperidone-loaded solid lipid nanoparticles (SLN): High pressure homogenization versus ultrasound. *Colloids Surfaces B Biointerfaces.* 2011; 86(1):158-165. doi:10.1016/j.colsurfb.2011.03.035.
36. Cevc G, Blume G, Schatzlein A. Transfersomes-mediated transepidermal delivery improves the regio-specificity and biological activity of corticosteroids in vivo1Dedicated to the late Dr. Henri Ernest Bodde.1. *J Control Release.* 1997; 45(3):211-226. doi:10.1016/S0168-3659(96)01566-0.
37. Ding J, Li J, Mao S. Development and evaluation of vinpocetine inclusion complex for brain targeting. *Asian J Pharm Sci.* 2015; 10:114-120. doi:10.1016/j.ajps.2014.08.008.
38. Duan Y, Wang J, Yang X, Du H, Xi Y, Zhai G. Curcumin-loaded mixed micelles: Preparation, optimization, physicochemical properties and cytotoxicity in vitro. *Drug Deliv.* 2015; 22(1):50-57. doi:10.3109/10717544.2013.873501.
39. Choi S G, Lee S-E, Kang B-S, Ng C L, Davaa E, Park J-S. Thermosensitive and Mucoadhesive Sol-Gel Composites of Paclitaxel/Dimethyl-β-Cyclodextrin for Buccal Delivery. Xu B, ed. *PLoS One.* 2014; 9(10):e109090. doi:10.1371/journal.pone.0109090.
40. Gilbert J C, Richardson J L, Davies M C, Palin K J, Hadgraft J. The effect of solutes and polymers on the gelation properties of pluronic F-127 solutions for controlled drug delivery. *J Control Release.* 1987; 5(2):113-118. doi:10.1016/0168-3659(87)90002-2.
41. García M C, Aldana A A, Tártara L I, et al. Bioadhesive and biocompatible films as wound dressing materials based on a novel dendronized chitosan loaded with ciprofloxacin. *Carbohydr Polym.* 2017; 175:75-86. doi:10.1016/j.carbpol.2017.07.053.
42. Karasulu E, Yavaoglu A, Evrenşanal Z, Uyanikgil Y, Karasulu H Y. Permeation studies and histological examination of sheep nasal mucosa following administration of different nasal formulations with or without absorption enhancers. *Drug Deliv.* 2008; 15(4):219-225. doi:10.1080/10717540802006377.
43. Yang C, Wu T, Qi Y, Zhang Z. Recent Advances in the Application of Vitamin E TPGS for Drug Delivery. *Theranostics.* 2018; 8(2):464-485. doi:10.7150/thno.22711.
44. Zhu H, Chen H, Zeng X, et al. Co-delivery of chemotherapeutic drugs with vitamin E TPGS by porous PLGA nanoparticles for enhanced chemotherapy against multidrug resistance. *Biomaterials.* 2014; 35(7):2391-2400. doi:10.1016/j.biomaterials.2013.11.086.
45. Muthu M S, Avinash Kulkarni S, Liu Y, Feng S-S. Development of docetaxel-loaded vitamin E TPGS micelles: formulation optimization, effects on brain cancer cells and biodistribution in rats. *Nanomedicine.* 2012; 7(3):353-364. doi:10.2217/nnm 11.111.
46. Chaudhary B, Verma S. Preparation and evaluation of novel in situ gels containing acyclovir for the treatment of oral herpes simplex virus infections. *Sci World J.* 2014; 2014:1-7. doi:10.1155/2014/280928.
47. Qian S, Wong Y C, Zuo Z. Development, characterization and application of in situ gel systems for intranasal delivery of tacrine. *Int J Pharm.* 2014; 468(1-2):272-282. doi:10.1016/j.ijpharm.2014.04.015.
48. Lindemann J, Leiacker R, Rettinger G, Keck T. Nasal mucosal temperature during respiration. *Clin Otolaryngol Allied Sci.* 2002; 27(3):135-139. doi:10.1046/j.1365-2273.2002.00544.x.
49. Proctor D F, Andersen I, Lundqvist G R. Human nasal mucosal function at controlled temperatures. *Respir Physiol.* 1977; 30(1-2):109-124. doi:10.1016/0034-5687(77)90025-1.
50. Jacky J P. Barometric measurement of tidal volume: effects of pattern and nasal temperature. *J Appl Physiol.* 1980; 49(2):319-325.
51. Wissing S A, Müller R H. The influence of solid lipid nanoparticles on skin hydration and viscoelasticity—In vivo study. *Eur J Pharm Biopharm.* 2003; 56(1):67-72. doi:10.1016/S0939-6411(03)00040-7.
52. Fang J Y, Fang C L, Liu C H, Su Y H. Lipid nanoparticles as vehicles for topical psoralen delivery: Solid lipid nanoparticles (SLN) versus nanostructured lipid carriers (NLC). *Eur J Pharm Biopharm.* 2008; 70(2):633-640. doi:10.1016/j.ejpb.2008.05.008.
53. Aboud H M, El Komy M H, Ali A A, El Menshawe S F, Abd Elbary A. Development, Optimization, and Evaluation of Carvedilol-Loaded Solid Lipid Nanoparticles for Intranasal Drug Delivery. *AAPS PharmSciTech.* 2016; 17(6):1-13. doi:10.1208/s12249-015-0440-8.

54. Guo Y, Luo J, Tan S, Otieno B O, Zhang Z. The applications of Vitamin e TPGS in drug delivery. *Eur J Pharm Sci.* 2013; 49(2):175-186. doi:10.1016/j.ejps.2013.02.006.
55. Beig A, Fine-Shamir N, Porat D, Lindley D, Miller J M, Dahan A. Concomitant solubility-permeability increase: Vitamin E TPGS vs. amorphous solid dispersion as oral delivery systems for etoposide. *Eur J Pharm Biopharm.* 2017; 121:97-103. doi:10.1016/j.ejpb.2017.09.012.
56. Yang C, Wu T, Qi Y, Zhang Z. Recent advances in the application of vitamin E TPGS for drug delivery. *Theranostics.* 2018; 8(2):464-485. doi:10.7150/thno.22711.
57. Ilium L. Nasal drug delivery—Possibilities, problems and solutions. In: *Journal of Controlled Release.* Vol 87.; 2003:187-198. doi:10.1016/S0168-3659(02)00363-2.
58. Graff C L, Pollack G M. Functional evidence for P-glycoprotein at the nose-brain barrier. *Pharm Res.* 2005; 22(1):86-93. doi:10.1007/s11095-004-9013-3.
59. Graff C L, Pollack G M. P-glycoprotein attenuates brain uptake of substrates after nasal instillation. *Pharm Res.* 2003; 20(8):1225-1230. doi:10.1023/A:1025053115583.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of enhancing cognition and/or memory in a subject in need thereof, comprising intranasally administering to the subject an in situ gelling composition comprising
    micelles formed with D-α-Tocopherol polyethylene glycol succinate (TPGS);
    vinpocetine encapsulated within the micelles; and
    a thermosensitive polymer,
    wherein the TPGS is 0.01-20% wt/volume,
    wherein the micelles are 10-100 nm in sized, and
    wherein the composition is an aqueous solution which forms a gel phase when said composition comes into contact with a surface at a temperature at or above 25° C.

2. The method of claim 1, wherein the thermosensitive polymer is poloxamer 407 which has a concentration of 20-25% w/v.

3. The method of claim 2, wherein the composition further comprises carbomers at a concentration of 0.2-0.7% w/v.

4. A method of treating a cognitive disorder in a subject in need thereof, comprising intranasally administering to the subject an in situ gelling composition comprising
    micelles formed with D-α-Tocopherol polyethylene glycol succinate (TPGS);
    vinpocetine encapsulated within the micelles; and
    a thermosensitive polymer,
    wherein the TPGS is 0.01-20% wt/volume,
    wherein the micelles are 10-100 nm in sized, and
    wherein the composition is an aqueous solution which forms a gel phase when said composition comes into contact with a surface at a temperature at or above 25° C.

5. The method of claim 4, wherein the cognitive disorder is selected from the group consisting of dementia, Huntington's disease, Parkinson's disease, and Alzheimer's disease.

6. The method of claim 4, wherein the thermosensitive polymer is poloxamer 407 which has a concentration of 20-25% w/v.

7. The method of claim 6, wherein the composition further comprises carbomers at a concentration of 0.2-0.7% w/v.

8. A method of treating a cerebrovascular disorder in a subject in need thereof, comprising intranasally administering to the subject an in situ gelling composition comprising
    micelles formed with D-α-Tocopherol polyethylene glycol succinate (TPGS);
    vinpocetine encapsulated within the micelles; and
    a thermosensitive polymer,
    wherein the TPGS is 0.01-20% wt/volume,
    wherein the micelles are 10-100 nm in sized, and
    wherein the composition is an aqueous solution which forms a gel phase when said composition comes into contact with a surface at a temperature at or above 25° C.

9. The method of claim 8, wherein the cerebrovascular disorder is selected from the group consisting of stroke, vertebral stenosis, intracranial stenosis, aneurysm, and a vascular malformation.

10. The method of claim 8, wherein the thermosensitive polymer is poloxamer 407 which has a concentration of 20-25% w/v.

11. The method of claim 10, wherein the composition further comprises carbomers at a concentration of 0.2-0.7% w/v.

12. An in situ gelling composition comprising
    micelles formed with D-α-Tocopherol polyethylene glycol succinate (TPGS);
    vinpocetine encapsulated within the micelles; and
    a thermosensitive polymer,
    wherein the TPGS is 0.01-20% wt/volume,
    wherein the micelles are 10-100 nm in sized, and
    wherein the composition is an aqueous solution which forms a gel phase when said composition comes into contact with a surface at a temperature at or above 25° C.

13. The in situ gelling composition of claim 12, wherein the thermosensitive polymer is poloxamer 407 which has a concentration of 20-25% w/v.

14. The in situ gelling composition of claim 13, wherein the composition further comprises carbomers at a concentration of 0.2-0.7% w/v.

* * * * *